(12) United States Patent
Cannon, Jr. et al.

(10) Patent No.: US 7,179,773 B2
(45) Date of Patent: Feb. 20, 2007

(54) FUNGICIDAL COMPOSITION

(75) Inventors: Harry B. Cannon, Jr., Shiloh, NC (US); Harry B. Cannon, III, Camden, NC (US); James Glessner, Diamond Lake, OR (US)

(73) Assignee: GSI Camden Products, LLC, Elizabeth City, NC (US)

(*) Notice: Subject to any disclaimer, the term of this patent is extended or adjusted under 35 U.S.C. 154(b) by 70 days.

(21) Appl. No.: 11/156,075

(22) Filed: Jun. 17, 2005

(65) Prior Publication Data

US 2006/0287218 A1    Dec. 21, 2006

(51) Int. Cl.
  *C11D 1/62*   (2006.01)
  *C11D 3/37*   (2006.01)

(52) U.S. Cl. .............. 510/199; 523/122; 428/907; 510/382; 510/384; 510/391; 510/398; 510/434; 510/466; 510/504; 510/421

(58) Field of Classification Search ............... 523/122; 428/907; 510/199, 382, 384, 391, 398, 434, 510/466, 504, 421
See application file for complete search history.

(56) References Cited

U.S. PATENT DOCUMENTS

| | | | |
|---|---|---|---|
| 4,866,106 A | 9/1989 | Pellow et al. | |
| 4,877,617 A * | 10/1989 | Namikoshi et al. | 424/409 |
| 4,990,547 A | 2/1991 | Stovicek | |
| 5,084,096 A | 1/1992 | Stovicek | |
| 5,096,488 A | 3/1992 | Stovicek | |
| 6,037,416 A * | 3/2000 | Iwamoto et al. | 525/207 |
| 6,242,440 B1 * | 6/2001 | De Witte et al. | 514/222.5 |
| 6,905,778 B2 * | 6/2005 | Tullos et al. | 428/480 |
| 2006/0167131 A1 * | 7/2006 | Mabey et al. | 523/122 |

* cited by examiner

*Primary Examiner*—Charles Boyer
(74) *Attorney, Agent, or Firm*—Chernoff, Vilhauer, McClung & Stenzel, LLP

(57) ABSTRACT

An improved, long-lasting aqueous-based fungicidal composition is disclosed.

10 Claims, No Drawings

FUNGICIDAL COMPOSITION

BACKGROUND OF THE INVENTION

Fungicidal coating compositions containing quaternary ammonium salts as the active ingredient in either polymeric emulsions or directly bonded to polymers are known. See U.S. Pat. Nos. 4,866,106, 4,990,547, 5,084,096 and 5,096,488. However, such compositions have fairly high quaternary ammonium content, are susceptible to chemical breakdown by exposure to UV light, do not adhere well to vertical surfaces, and tend to leach out the active ingredient rather rapidly due to the exposure to salt water and rain and washing. There is therefore a need in the art for a fungicidal composition that has a lower quaternary ammonium content, that is chemically stable, that adheres well to vertical surfaces, and that is resistant to active ingredient washout. These needs are met by the present invention, which is summarized and described in detail below.

BRIEF SUMMARY OF THE INVENTION

According to the present invention there is provided an improved fungicidal coating composition that is long-lasting, suitable for vertical surface applications, chemically stable, and highly resistant to active ingredient washout. The composition of the invention incorporates a fungicidal quaternary ammonium compound, an improved copolymer latex containing a nonionic surfactant for stabilization, and a UV absorber to protect the coating and the treated surface from radiation damage. It may also incorporate a silicone latex to provide an additional barrier against moisture. The resulting mixture, which can be supplied as a concentrated product or diluted to final application strength, exhibits a broad range of activity against molds and fungi. A further feature of the invention is that the use of a nonionic surfactant stabilizer with the copolymer latex surprisingly reduces the amount of quaternary ammonium compound required to achieve protection, which reduces both environmental impact of the composition and the hazards of handling the composition.

The coating composition of the invention is particularly well-suited for the long term protection of wood, concrete, stucco, masonry and drywall surfaces from growth of mildew and fungus, offering protection for periods from about one to about five years.

The foregoing and other objectives, features, and advantages of the invention will be more readily understood upon consideration of the following detailed description of the invention taken in conjunction with the accompanying drawings.

DETAILED DESCRIPTION OF PREFERRED EMBODIMENTS

In a first aspect, the invention comprises a three-component aqueous-based fungicidal coating composition of (1) at least one quaternary ammonium compound; (2) a stabilized copolymer latex; and (3) an ultraviolet light (UV) absorber.

In a second aspect, the invention comprises the aforesaid three-component composition with a fourth water-resistant component (4) of a silicone latex polymer.

As used in the specification and claims, the term "about" means the specified value +10% of that value.

Exemplary materials suitable for use as the above four components follow.

Component (1) may be a dialkyl dimethyl ammonium compound with or without an alkylbenzyl dimethyl ammonium compound. Specific examples of dialkyl dimethyl ammonium compounds are dioctyl dimethyl ammonium chloride, didecyl dimethyl ammonium chloride (DDAC), didodecyl dimethyl ammonium chloride, octyldecyl dimethyl ammonium chloride, decyldodecyl dimethyl ammonium acetate, and dihexadecyl dimethyl ammonium acetate. Examples of alkylbenzyl dimethyl ammonium compounds are decylbenzyl dimethyl ammonium chloride, decylchlorobenzyl dimethyl ammonium chloride, and dodecyldichlorobenzyl dimethyl ammonium acetate. A preferred dialkyl dimethyl ammonium compound is DDAC in a water/ethanol mixture, commercially available as Bardac 2250 (50 wt % actives) and Bardac 2280 (80 wt % actives) from Lonza, Inc. of Fair Lawn, N.J. A preferred alkylbenzyl dimethyl ammonium compound is alkyl (C12–C18) benzyl dimethyl ammonium chloride in a water/ethanol mixture, also commercially available from Lonza as Barquat 1552.

Component (2) is a vinyl acetate/octyl maleate latex copolymer stabilized with from about 0.05 to about 1.0 wt % of a nonionic surfactant such as an octylphenyl ethoxylate, commercially available as RayVace 530 (containing 52 wt % latex solids content) from Specialty Polymers, Inc. of Woodburn, Oreg.

Component (3) may be micronized zinc oxide (available as Zinc Oxide Transparent from LanXess Corporation of Pittsburg, Pa.) or titanium dioxide (available as UV-Titan L-181 from Kemira Pigments Company of Pori, Finland) having a mean particle diameter on the order of 0.5 micron.

Component (4) is preferably a hydroxyl-terminated dimethyl siloxane-and amorphous silica-containing aqueous emulsion containing 1–5 wt % aminomethylpropanol, commercially available as Dow Corning® 84 Additive (containing 40–70 wt % actives, balance water) from Dow Corning Corporation of Midland, Mich.

The components of the inventive coating composition may be mixed in conventional fashion to produce a concentrate having a make-up in terms of wt % active components of (1) a quaternary ammonium compound content of from about 0.5 to about 25 wt %; (2) a latex copolymer content of from about 1.0 to about 40 wt %; (3) a UV absorber content of from about 0.5 to about 12 wt %; and balance water. Optional component (4) may be present from about 0 to about 20 wt %. The concentrate is preferably diluted with water prior to application.

A particularly preferred composition in terms of wt % active ingredients is (1) about 12 wt % quaternary ammonium compound, preferably DDAC; (2) about 36 wt % latex copolymer; (3) from about 4 to about 6 wt % titanium dioxide; and balance water. Optional component (4) is preferably present in the amount of from about 4 to about 7 wt %.

EXAMPLE 1

The above preferred composition may be prepared on a laboratory scale as follows.

1. Place 2750 g of RayVace 530 (52 wt % latex solids content, balance water) in a five-liter mixing vessel equipped with an impeller capable of mixing the vessel's contents at 30–300 rpm. Plastic or glass-lined vessels are preferred.

2. In a separate one-liter mixing vessel equipped with a high speed impeller capable of mixing speeds of up to 3000 rpm place 597 g of Bardac 2280 (80 wt % active ingredients, 20 wt % mixture of 50/50 w/w ethanol/water) and 238 g of TiO2 (UV-Titan L-181). Disperse the TiO2 until a uniform suspension is obtained.

3. Add 387 g of water to the RayVace 530 latex with slow mixing at 100–300 rpm.

4. Once the latex has been diluted and the titanium dioxide has been dispersed thoroughly into the Bardac 2280, add the Bardac 2280/titanium dioxide suspension into the vortex of the latex solution sufficiently slowly that no precipitation or coagulation occurs.

If the Dow Corning® 84 Additive is to be used as waterproofing agent, 387 g of that additive (containing 70 wt % active ingredients) should replace the 387 g of water in step 3 above.

The so-made composition is preferably diluted using sufficient water to produce a final DDAC content of from about 0.5 to about 1.0 wt %. It can then be applied to the surface to be treated by dipping the article or by brushing or mopping or spraying it onto the surface. If dipping is used, an immersion time of from about 30 to about 60 seconds will ensure adequate surface absorption of the product. If the composition is sprayed, appropriate precautions against inhalation should be taken.

EXAMPLES 2–12

Batches of the inventive composition were prepared as in Example 1 and diluted with 12 parts water to obtain the concentrations of the components noted in Table 1 below, then applied to samples of wood and gypsum board infused with fungal spores, according to the following protocol.

Douglas fir sapwood samples (10×20×40 mm long) were sawn from freshly sawn lumber and frozen until needed. Gypsum board samples (25×25×12 mm thick) were cut from commercially available material and soaked in water for 30 minutes prior to treatment.

Mold chambers for the wood and gypsum board consisted of 115 mm diameter glass Petri dishes. Two pieces of filter paper were placed on the bottom and distilled water was added until a small amount of excess water was visible on the paper surface. A single u-shaped glass rod was placed on the filter paper.

The wood and gypsum samples were treated by immersion for 30 seconds in the diluted compositions of the invention. The samples were allowed to drain, then placed on the glass rod in the Petri dish. Each composition was tested on 9 wood wafers and 9 gypsum boards. As a control (C), two sets of wood and gypsum samples were not treated. The samples were then sprayed with a mixture of fungal spores and hyphae obtained from the surfaces of heavily molded Douglas fir lumber. Previous assays of the lumber suggested that the fungi present included species in the genera Graphium, Penicillium, Aspergillus, and Trichoderma.

The plates were sealed with wax film to retard drying and incubated at room temperature (20°–23° C.) for 4 weeks, after which the individual samples were visually assessed for the degree of fungal discoloration on a scale from 0 (no discoloration) to 100% (complete discoloration). The evaluation for the gypsum samples included fungal growth on both the exposed gypsum surface and on the paper backing. The results are set forth in Table 2 and represent mean values for each batch of 9 samples.

TABLE 1

| Ex. No. | Ray Vace 530 (wt %) | DDAC (wt %) | TiO2 (wt %) | Dow Corning 84 (wt %) |
|---|---|---|---|---|
| C | 0 | 0 | 0 | 0 |
| 2 | 2.0 | 0.5 | 0.5 | 0 |
| 3 | 2.0 | 1.0 | 0.5 | 0 |
| 4 | 2.0 | 1.0 | 0.5 | 1.0 |
| 5 | 2.5 | 0.5 | 0.5 | 0 |
| 6 | 2.5 | 1.0 | 0.5 | 0 |
| 7 | 2.5 | 1.0 | 0.5 | 1.0 |
| 8 | 2.0 | 2.0 | 0.5 | 0 |
| 9 | 3.0 | 0.5 | 0.5 | 0 |
| 10 | 3.0 | 0.5 | 0.5 | 1.0 |
| 11 | 3.0 | 1.0 | 0.5 | 0 |
| 12 | 3.0 | 1.0 | 0.5 | 1.0 |

TABLE 2

| | Degree of Fungal Discoloration (%) | |
|---|---|---|
| Ex. No. | Wood | Gypsum |
| C | 68 | 50 |
| 2 | 13 | 5 |
| 3 | 10 | 10 |
| 4 | 7 | 0 |
| 5 | 16 | 5 |
| 6 | 4 | 0 |
| 7 | 6 | 0 |
| 8 | 34 | 10 |
| 9 | 13 | 10 |
| 10 | 6 | 10 |
| 11 | 10 | 20 |
| 12 | 18 | 0 |

As is apparent from the results in Table 2, the inventive composition is an effective antifungal agent. And as can be seen from a comparison of Example 8 with Examples 9 and 10, the use of a higher stabilized latex content (3.0 wt %) rather surprisingly permits the use of a much lower DDAC content (0.5 wt %) and yet yields far superior results on wood.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

We claim:

1. A fungicidal composition comprising the components
   (i) at least one quaternary ammonium compound;
   (ii) a vinyl acetate/octyl maleate copolymer latex stabilized with an octylphenyl ethoxylate nonionic surfactant;
   (iii) a UV absorber, and
   (iv) water.

2. The composition of claim 1 wherein component (i) is selected from the group consisting of dialkyl dimethyl ammonium salts and alkylbenzyl dimethyl ammonium salts; and component (iii) is selected from the group consisting of zinc oxide and titanium dioxide.

3. The composition of claim 1 wherein component (i) is selected from the group consisting of dialkyl dimethyl ammonium chloride, alkylbenzyl dimethyl ammonium chloride and mixtures thereof; component (ii) contains from about 0.5 to about 1.0 wt % of said nonionic surfactant; and component (iii) is titanium dioxide having a mean particle diameter of about 0.5 micron.

4. The composition of claim 3 wherein component (i) is didecyl dimethyl chloride.

5. The composition of claim 4 wherein the components are present in the following weight percentages:
component (i) from about 0.5 to about 25 wt %;
component (ii) from about 1.0 to about 40 wt %; and
component (iii) from about 0.5 to about 12 wt %.

6. The composition of claim 5 optionally including a further component (v) of an aqueous emulsion comprising hydroxyl-terminated dimethyl siloxane, amorphous silica and aminomethylpropanol, said component (v) being present in an amount of from about 0 to about 20 wt %.

7. The composition of claim 6 wherein the components are present in the following approximate weight percentages:
component (i) about 12 wt %;
component (ii) about 36 wt %;
component (iii) from about 4 to about 6 wt %; and
component (v) from about 5 to about 7 wt %.

8. The composition of claim 7 diluted with water.

9. The composition of claim 8 wherein the dilution is with from about 10 to about 15 parts water.

10. The composition of claim 9 wherein the dilution is with about 12 parts water.

* * * * *